United States Patent
Xie et al.

(10) Patent No.: US 10,126,245 B1
(45) Date of Patent: Nov. 13, 2018

(54) METHOD FOR REPRESENTING QUALITY CHANGE PROCESS OF BEEF FAT DURING REPEATED FREEZING AND THAWING THROUGH RAMAN SPECTRUM

(71) Applicant: Jiangnan University, Wuxi (CN)

(72) Inventors: Yunfei Xie, Wuxi (CN); Qingmin Chen, Wuxi (CN); Weirong Yao, Wuxi (CN); Yahui Guo, Wuxi (CN); Yuliang Cheng, Wuxi (CN); He Qian, Wuxi (CN)

(73) Assignee: Jiangnan University, Wuxi (CN)

( * ) Notice: Subject to any disclaimer, the term of this patent is extended or adjusted under 35 U.S.C. 154(b) by 0 days.

(21) Appl. No.: 15/815,297

(22) Filed: Nov. 16, 2017

(30) Foreign Application Priority Data

Jul. 31, 2017 (CN) .......................... 2017 1 0639358

(51) Int. Cl.
| | |
|---|---|
| *G01J 3/44* | (2006.01) |
| *G01N 21/65* | (2006.01) |
| *G01N 33/03* | (2006.01) |
| *G01N 33/12* | (2006.01) |
| *G01N 1/28* | (2006.01) |

(52) U.S. Cl.
CPC ............. *G01N 21/65* (2013.01); *G01N 1/286* (2013.01); *G01N 33/03* (2013.01); *G01N 33/12* (2013.01)

(58) Field of Classification Search
CPC ........ G01J 3/02; G01J 3/44; G01N 2021/656; G01N 21/65; G01N 21/658
USPC ......................................................... 356/301
See application file for complete search history.

(56) References Cited

U.S. PATENT DOCUMENTS

| | | | | |
|---|---|---|---|---|
| 2006/0119853 | A1* | 6/2006 | Baumberg | G01N 21/658 356/445 |
| 2012/0327417 | A1* | 12/2012 | Amako | G01N 21/658 356/445 |
| 2013/0176562 | A1* | 7/2013 | Shioi | G01J 3/4412 356/301 |
| 2016/0199497 | A1* | 7/2016 | Cheng | A61K 49/008 514/517 |

(Continued)

FOREIGN PATENT DOCUMENTS

| | | | | |
|---|---|---|---|---|
| KR | 20120099939 A | * | 9/2012 | |
| WO | WO 2017021253 A1 | * | 2/2017 | ............. G01N 33/12 |

*Primary Examiner* — Md M Rahman
(74) *Attorney, Agent, or Firm* — Wang Law Firm, Inc.

(57) ABSTRACT

A method for representing the quality change process of beef fat during repeated freezing and thawing through a Raman spectrum. The method comprises the steps of (1) setting operating parameters of a laser Raman spectrometer, wherein the operating parameters include the wavelength of exciting light, the laser power and the scanning time; (2) repeatedly freezing and thawing beef, extracting fat in the thawed beef, and then conducting Raman spectrum scanning on the extracted fat; (3) analyzing and processing an obtained original Raman spectrum, so that the quality change process of beef fat during repeated freezing and thawing is represented. The Raman spectrum is used for monitoring the quality change process of beef fat during repeated freezing and thawing, the method is flexible and simple, the analysis speed is high, and the fat quality of beef which is repeatedly frozen and thawed can be represented efficiently and accurately; in addition, analysis solvent consumption is low, and the detection cost is low.

8 Claims, 4 Drawing Sheets

(56) References Cited

U.S. PATENT DOCUMENTS

2017/0196922 A1* 7/2017 Embree .................. A61K 35/74

* cited by examiner

METHOD FOR REPRESENTING QUALITY CHANGE PROCESS OF BEEF FAT DURING REPEATED FREEZING AND THAWING THROUGH RAMAN SPECTRUM

BACKGROUND OF THE INVENTION

Technical Field

The invention relates to a method for detecting the quality change process of beef during repeated freezing and thawing, in particular to a method for representing deterioration of the fat quality of beef during the repeated freezing and thawing process through a Raman spectrum.

Description of Related Art

Beef belongs to high-protein and high-fat food and deteriorates extremely easily in the chemical and enzymatic promoting process. Therefore, freeze storage is still the main preservation method the meat and meat product which is most widely used for long-distance transportation at present. The quality of products can be well maintained in freeze storage and the shelf life of the products is long. Due to the fact that an existing cold-chain transportation system in China is poor, beef is prone to being repeatedly frozen and thawed in China. It is proved by numerous studies that deterioration of the quality, the flavor, the color, the microbial activity and the nutritional value of meat is accelerated by repeated freezing and thawing. Most researchers think that the main reason for meat quality deterioration caused by repeated freezing and thawing lies in formation of ice crystals in the freezing process. Breakage of cell membranes is caused by the formed ice crystals, consequentially, the main catalyst used for catalyzing lipid oxidation in cells is released, and lipid oxidation is accelerated. However, many fat oxidation products such as hydrocarbon, aldehyde and ketone can easily cause quality changes, such as peculiar smells, rancidification, color deterioration and protein oxidation, of beef.

Existing indexes about fat quality evaluation mainly include the peroxide value, Thiobarbituric Acid Reactive Substances (TBARS), the acid value and the like. The main detection methods include efficient liquid-phase chromatography, chemiluminescent immunoassay, a fluorescence detection method and the like, however, a large quantity of reagents and consumables are required by the methods, sample pretreatment is complex, and the analysis time is long.

BRIEF SUMMARY OF THE INVENTION

The invention mainly aims to provide a method for representing the quality change process of beef fat during repeated freezing and thawing through a Raman spectrum, and the method has the characteristics of easy and convenient operation, rapid analysis and the like and thus overcomes the defects in the prior art.

For achieving the above purpose, the following technical scheme is adopted by the invention:

The embodiment of the invention provides a method for representing the quality change process of beef fat during repeated freezing and thawing through a Raman spectrum, and the method comprises the steps:

(1) setting operating parameters of a laser Raman spectrometer, wherein the operating parameters include the wavelength of exciting light, the laser power and the scanning time;

(2) repeatedly freezing and thawing beef, then extracting fat in the thawed beef, and afterwards conducting Raman spectrum scanning on the extracted fat; and (3) analyzing and processing an obtained original Raman spectrum, so that the quality change process of the beef fat during repeated freezing and thawing is represented.

In certain specific embodiments, the wavelength of the exciting light in the step (1) is set to 785 nm, the laser power is set to 50~500 mw, and the scanning time is set to 5~20 s.

In certain specific embodiments, in the process of repeatedly freezing and thawing the beef in the step (2), the beef is frozen for over 24 h at the temperature of −18~−20 DEG C. and then is thawed at the temperature of 2~4 DEG C. till the center temperature of the beef reaches 2~4 DEG C., so that one freezing and thawing cycle is completed (the thawing time is generally over 20 h).

In certain specific embodiments, the step (2) comprises the sub-steps of mincing the thawed beef, mixing and oscillating an extraction agent and the minced beef overnight, and then removing the extraction agent through rotary evaporation to extract the fat, wherein the extraction agent includes petroleum ether.

In certain specific embodiments, the step (3) comprises the sub-step of conducting background deduction on the obtained original Raman spectrum, and conducting normalization through the Raman peak 1442 $cm^{-1}$, so that a normalized Raman spectrum is obtained.

In certain specific embodiments, the step (3) further comprises the sub-step of measuring the changes of the peak intensities of selected characteristic peaks in the normalized Raman spectrum, so that the quality change process of the beef fat during repeated freezing and thawing is represented. Wherein, the peak intensities of the characteristic peak 970 $cm^{-1}$, the characteristic peak 1080 $cm^{-1}$ and the characteristic peak 1655 $cm^{-1}$ are decreased gradually along with the increment of the number of freezing and thawing times of the beef, and the peak intensities of the characteristic peak 1068 $cm^{-1}$ and the characteristic peak 1125 $cm^{-1}$ are increased gradually along with the increment of the number of freezing and thawing times of the beef.

Furthermore, the selected characteristic peaks include the characteristic peak 970 $cm^{-1}$, the characteristic peak 1080 $cm^{-1}$, the characteristic peak 1068 $cm^{-1}$, the characteristic peak 1125 $cm^{-1}$, the characteristic peak 1655 $cm^{-1}$, characteristic peak 1745 $cm^{-1}$.

In certain specific embodiments, the step (3) further comprises the sub-step of measuring the changes of selected peak intensity ratios in the normalized Raman spectrum, so that the quality change process of the beef fat during repeated freezing and thawing is represented. Wherein, $I_{1655}/I_{1745}$ and $I_{1655}/I_{1442}$ are decreased gradually along with the increment of the number of freezing and thawing times of the beef.

Furthermore, the selected peak intensity ratios include $I_{1655}/I_{1745}$ and $I_{1655}/I_{1442}$, wherein $I_{1655}$ is the peak intensity of the Raman peak 1655 $cm^{-1}$, $I_{1745}$ is the peak intensity of the Roman peak 1745 $cm^{-1}$, $I_{1442}$ is the peak intensity of the Roman peak 1442 $cm^{-1}$.

Compared with the prior art, the Raman spectrum is adopted by the invention for monitoring the quality change process of beef fat during repeated freezing and thawing, the method is flexible and simple, the analysis speed is high, and the fat quality of beef which is frozen and thawed repeatedly can be represented efficiently and accurately; in addition, analysis solvent consumption is low, and the detection cost is low.

DETAILED DESCRIPTION OF THE INVENTION

Figure 1A:
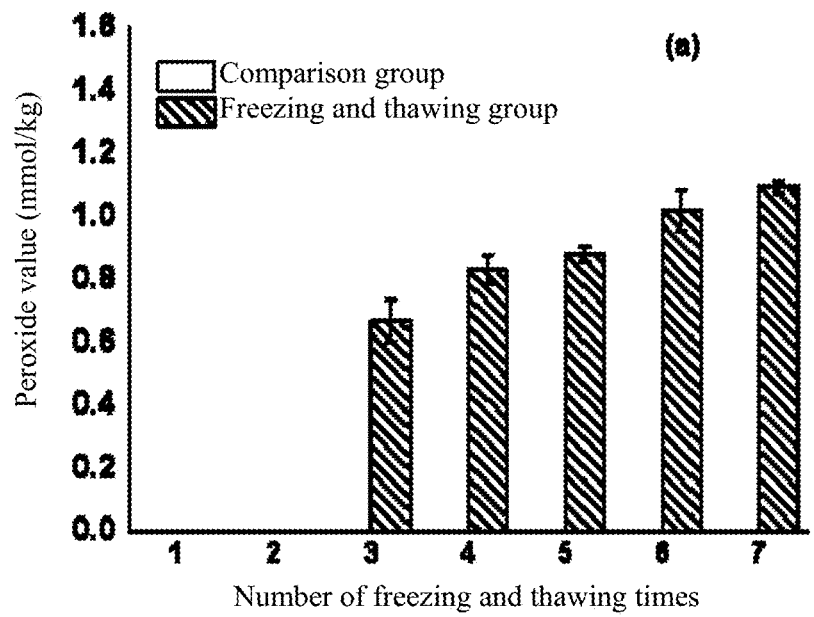
FIGS. 1a-1c respectively show the changes of the peroxide value, the TBARS and the acid value of fat in beef which is repeatedly frozen and thawed by different times in one embodiment of the invention.

As mentioned above, for overcoming the defects of the prior art, the inventor puts forwards the technical scheme of the invention through lone-term study and mass practices, and a method for representing the quality change process of beef fat during repeated freezing and thawing through a Raman spectrum is mainly provided. Generally speaking, the method comprises the first step of setting parameters of a Raman spectrometer and scanning conditions, the second step of analyzing and processing the Raman spectrum, and the third step of determining characteristic peaks and spectrum data which can represent the quality change process of beef fat during repeated freezing and thawing in the Raman spectrum. According to the method of the invention, the detection speed is high, analysis solvent consumption is low, the detection cost is low, and the fat quality of beef which is frozen and thawed repeatedly can be represented rapidly.

In certain specific embodiments, the method for representing the quality change process of beef fat during repeated freezing and thawing comprises the following steps:

(1) determination of detection conditions:
setting of parameters of a laser Raman spectrometer;
(2) sample detection:
a. repeatedly freezing and thawing beef, and extracting fat in the thawed beef;
b. conducting Raman spectrum scanning on the extracted fat;
(3) processing of spectrum data
analyzing and processing an obtained original Raman spectrum correspondingly.

Furthermore, in the step (1), the parameters of the laser Raman spectrometer can be set as: The wavelength of an exciting light source is 785 nm, the laser power of the spectrometer is 50~300 mw, and the scanning time is 5~20 s.

Furthermore, the step (2a) comprises the sub-steps of repeatedly freezing and thawing beef (specifically, the beef is frozen for over 24 h at the temperature of –18~–20 DEG C. and then is thawed at the temperature of 2~4 DEG C. till the center temperature of the beef reaches 2~4 DEG C., so that one freezing and thawing cycle is completed, for example, the beef is frozen for over 24 h at the temperature of –20 DEG C. and then is thawed for over 20 h at the temperature of 4 DEG C., so that one freezing and thawing cycle is completed); mincing the thawed beef, mixing the extraction agent such as petroleum ether (with the boiling point of 30~60 DEG C.) with the minced beef, placing the mixture of the extraction agent and the minced beef on a table concentrator so as to be oscillated overnight, and then recovering the petroleum ether through a vacuum rotary evaporator, so that fat is obtained.

Furthermore, the step (2a) comprises the sub-step of conducting Raman spectrum scanning, so that an original Raman spectrum of the beef fat is obtained. Multiple points, such as five points, are selected for each sample for obtaining Raman spectrum data.

Furthermore, the step (3) comprises the sub-steps:
a. conducting background deduction, and conducting normalization through the Raman peak 1442 cm$^{-1}$ ($\delta(CH_2)$), so that a normalized Raman spectrum is obtained;
b. determining characteristic peaks representing the quality change process of the beef fat during repeated freezing and thawing in the spectrum, wherein the characteristic peaks mainly include the characteristic peak 970 cm$^{-1}$ ($\gamma$(=C—H)), the characteristic peak 1080 cm$^{-1}$ ($\nu$(C—C)), the characteristic peak 1068 cm$^{-1}$ ($\nu$(C—C)), the characteristic peak 1125 cm$^{-1}$, the characteristic peak 1655 cm$^{-1}$ ($\nu$(C=C)) and the characteristic peak 1745 cm$^{-1}$ ($\nu$(C=O));
c. determining the changes of peak intensities representing the quality change process of the beef fat during repeated freezing and thawing of the spectrum, and the peak intensities mainly include $I_{1655}/I_{1745}$ and $I_{1655}/I_{1442}$.

Wherein, the peak intensities of the characteristic peak 970 cm$^{-1}$, the characteristic peak 1080 cm$^{-1}$ and the characteristic peak 1655 cm$^{-1}$ are decreased gradually along with the deterioration of the fat quality, however, the peak intensities of the characteristic peak 1068 cm$^{-1}$ and the characteristic peak 1125 cm$^{-1}$ are increased gradually along with the deterioration of the fat quality. The intensity peak change of the characteristic peak 1655 cm$^{-1}$ is the most remarkable.

Meanwhile, $I_{1655}/I_{1745}$ and $I_{1655}/I_{1442}$ are decreased gradually along with the increment of the number of freezing and thawing times of the beef.

A further detailed description of the technical scheme of the invention is given as follows with embodiments and accompanying drawings, however, the invention is not only limited to the following embodiments.

In the following embodiment, beef is sliced (4 cm*4 cm*4 cm), packaged and frozen firstly. The beef is frozen for over 24 h at the temperature of –20 DEG C. and then thawed at the temperature of 4 DEG C. for over 20 h, so that one freezing and thawing cycle is completed.

In the following embodiment, the following detection conditions are adopted.

Parameters of the laser Raman spectrometer are set as: the wavelength of an exciting light source is 785 nm, the laser power is 50~300 mw, and the scanning time is 5~20 S.

Of course, those skilled in the field can also set other parameters of the laser Raman spectrometer according to learning materials.

After the detection conditions are determined, Raman spectrum processing can be conducted according to the following method:

Conducting baseline correction on the original Raman spectrum obtained by scanning a sample, and then conducting normalization through the Raman peak of 1442 cm$^{-1}$, so that a normalized Raman spectrum is obtained.

In the following embodiment, raw beef is frozen and thawed for seven freezing and thawing cycles (short for freezing and thawing group), the completely-thawed beef is minced, petroleum ether (with the boiling point of 30~60 DEG C.) is mixed with the minced beef, the mixture of the petroleum ether and the minced beef is placed on a table concentrator so as to be oscillated overnight, the petroleum ether is recovered through a vacuum rotary evaporator, and thus fat is obtained.

Raman spectrum scanning is conducted on the obtained fat, so that the original Raman spectrum of the beef fat is obtained. Five points are selected for each sample for obtaining Raman spectrum data. The spectrum is processed in the way mentioned above.

Meanwhile, in the embodiment, the quality change process of beef fat during repeated freezing and thawing is detected and verified with the peroxide value, the TBARS and the acid value as the evaluation indexes.

Wherein, the peroxide value is measured according to the method GB5009.227-2016, specifically:

a beef sample with the weight of 2 g-3 g (accurate to 0.001 g) is placed in an iodine flask with the volume of 250 mL, 30 mL of mixed liquor of trichloromethane and ice acetic acid liquor (with the volume ratio being 40:60) is added, and the iodine flask is oscillated slightly to make fat be completely dissolved. 1.00 mL of the saturated potassium iodide solution is added accurately, the flask cap is tightly screwed, and the iodine flask is oscillated slightly for 0.5 min and placed in a dark place for 3 min. The iodine flask is taken out from the dark place, then 100 mL of water is added into the iodine flask, after uniform oscillation, separated-out iodine is titrated instantly with a sodium thiosulfate standard solution (the standard solution with the concentration of 0.002 mol/L is used when the estimated peroxide value is 0.15 g/100 g or below, and the standard solution with the concentration of 0.01 mol/L is used when the estimated peroxide value is over 0.15 g/100 g), 1 mL of the starch indicator with the concentration of 1% is added when the iodine is titrated to be faint yellow, and titration continues to be conducted and violent oscillation is conducted till the blue color of the solution disappears. Meanwhile, a blank test is conducted. The volume $V_0$ of the sodium thiosulfate solution consumed by the blank test cannot be over 0.1 mL.

$$X_1(\text{mmol/kg}) = C \times (V-V0) \times 0.1269 \times 100/m$$

$X_1$—the peroxide value, unit: g/100 g
V—the volume of the sodium thiosulfate standard solution consumed by the sample, unit: mL
$V_0$—the volume of the sodium thiosulfate standard solution consumed by the blank test, unit: mL
c—the concentration of the sodium thiosulfate standard solution, unit: mol/L
0.1269—the mass of iodine corresponding to 1.00 mL of the sodium thiosulfate standard titration solution [c(Na2S2O3)=1.000 mol/L]
m—mass of the sample, unit: g
100—the conversion coefficient Measurement of TBARS: a beef sample with the weight of 5 g and 10 mL of TCA-EDTA (0.1%) with the concentration of 7.5% are mixed and then homogenated at a high speed, filtering is conducted, 5 ml of supernate is obtained, and 5 ml of the TBA solution (with the concentration of 2.88 g/L) is added. The beef sample is taken out after being water-bathed in a boiling water bath for 40 min and is placed under the room temperature so as to be cooled. Afterwards, reaction liquid is transferred into a clean colorimetric tube, 5 ml of chloroform is added, oscillating is conducted, supernate is obtained after standing and layering, ultraviolet detection is conducted, and thus the light absorption value at the position with the wavelength of 532 nm is obtained. A standard curve is drawn based on tetraethoxypropane.

The acid value is measured according to the method GB5009.229-2016, specifically:

A conical flask with the volume of 250 mL is obtained, 50 mL~100 mL of mixed liquor of ethyl ether and isopropyl alcohol (with the volume ratio being 1:1) and 3-4 drops of the phenolphthalein indicator are added based on a sample with the weight being about 10 g and with m as the mass unit, and the sample is dissolved through sufficient oscillation. Then titration is conducted with a standard titration solution with the concentration of 0.1 mol/L, and titration is ended when the sample solution turns reddish and does not obviously fade in 15 s. Titration is stopped immediately, the milliliter quantity of the standard titration solution consumed for titration is recorded, and the numerical value of the milliliter quantity is V.

Another conical flask with the volume of 250 mL is obtained, the same organic solvent mixed liquor and the same indicator with the same volumes as those for sample measurement mentioned above are accurately added, and oscillation and even mixing are conducted. Then titration is conducted with a standard titration solution with the concentration of 0.1 mol/L, and titration is ended when the sample solution turns reddish and does not obviously fade in 15 s. Titration is stopped immediately, the milliliter quantity of the standard titration solution consumed for titration is recorded, and the numerical value of the milliliter quantity is $V_0$.

$$X_{AV} = (V-V0)*c*56.11/m$$

$X_{AV}$—the acid value, unit: mg/g
V—the volume of the standard titration solution consumed for sample measurement, unit: mL
$V_0$—the volume of the standard titration solution consumed for the corresponding blank test, unit: mL
c—the molar concentration of the standard titration solution, unit: mol/L
56.1—the molar mass of potassium hydroxide, unit: g/mol
m—the weight of the fat sample, unit: g If the acid value is smaller than or equal to 1 mg/g, and two decimal places are reserved for the calculation result; if 1 mg/g<acid value≤100 mg/g, one decimal place is reserved for the calculation result; if the acid value is larger than 100 mg/g, the integer is reserved for the calculation result.

In addition, each freezing and thawing cycle is compared with a corresponding comparison group (beef in the frozen state all the time), and other experiment conditions of the comparison groups are the same as those of the freezing and thawing groups.

Figure 1B:
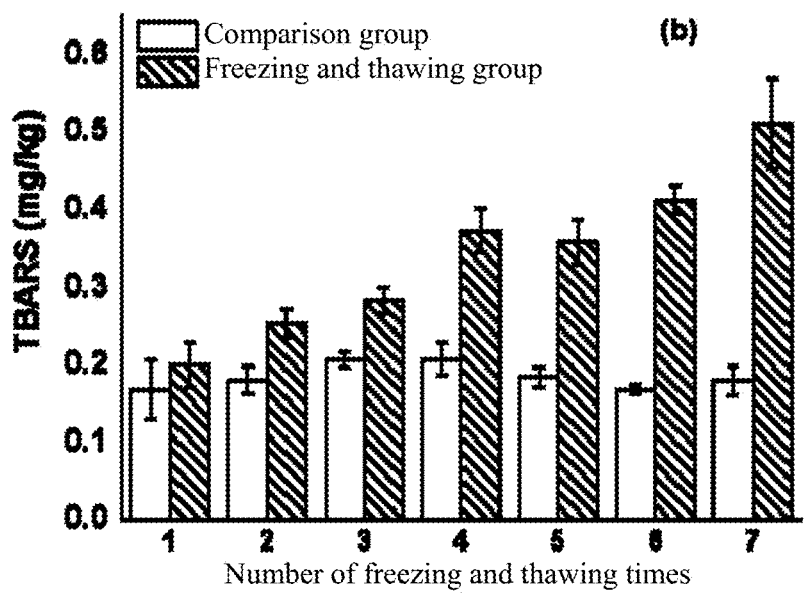
Figure 1C:
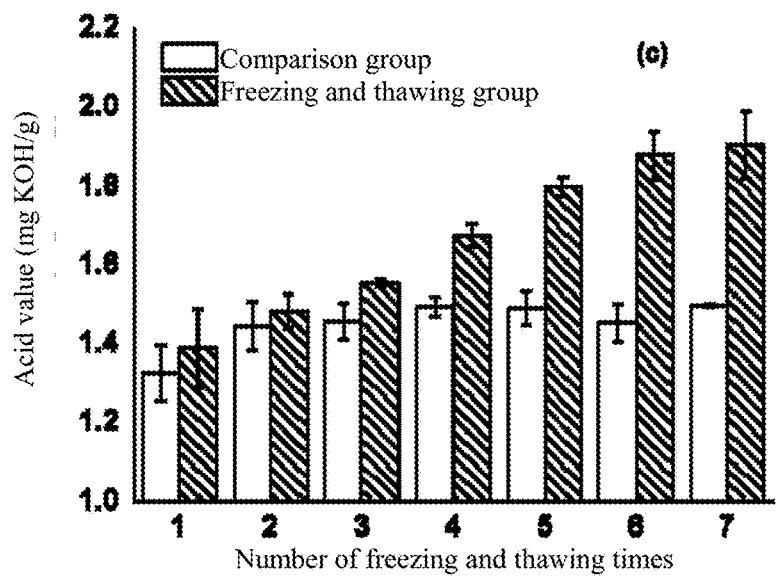
Figure 2A:
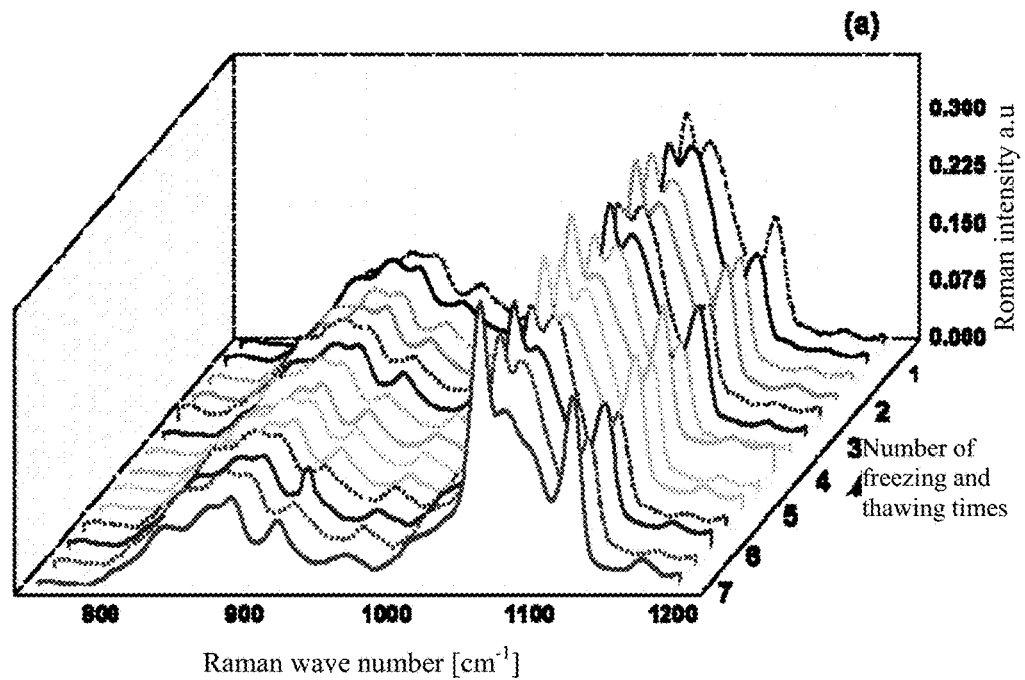
FIGS. 2a-2b respectively show Raman spectrum changes of fat in beef which is repeatedly frozen and thawed by different times within the range of 750-1200 cm$^{-1}$ and the range of 1600-1800 cm$^{-1}$ in one embodiment of the invention.
Figure 2B:
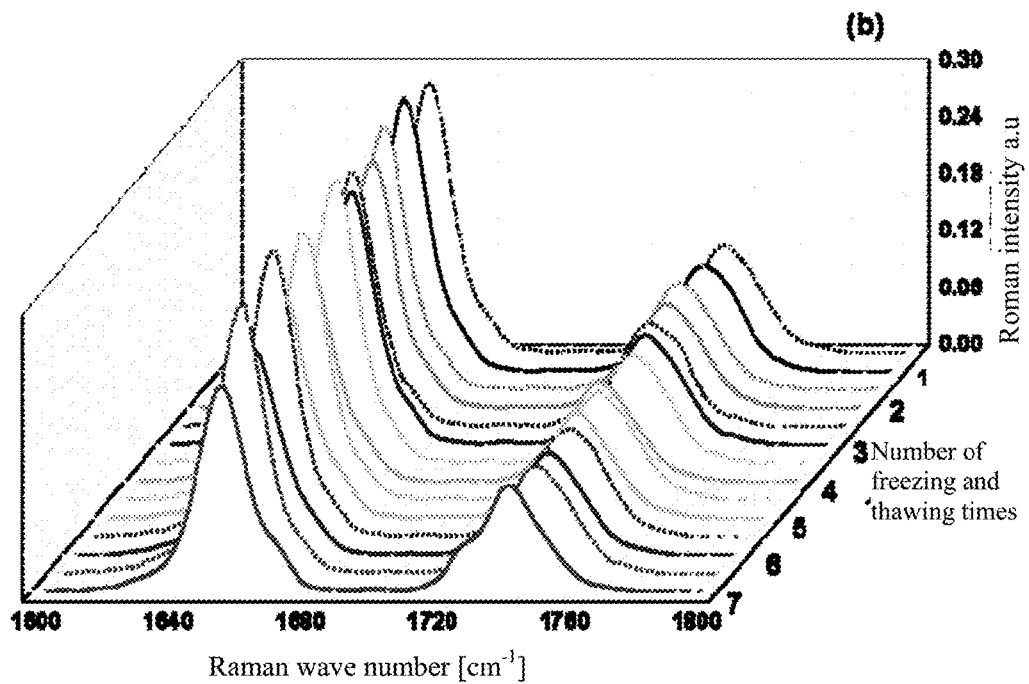
Figure 3A:
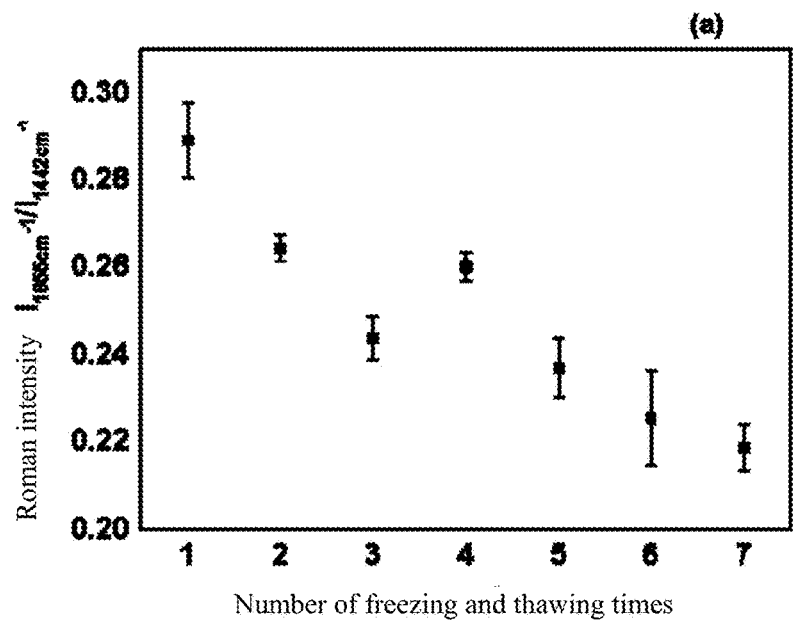
FIGS. 3a-3b respectively show the peak intensity ratio $I_{1655}/I_{1745}$ and the peak intensity ratio $I_{1655}/I_{1442}$ of the Raman spectrum of fat in beef which is repeatedly frozen and thawed by different times in one embodiment of the invention.
Figure 3B:
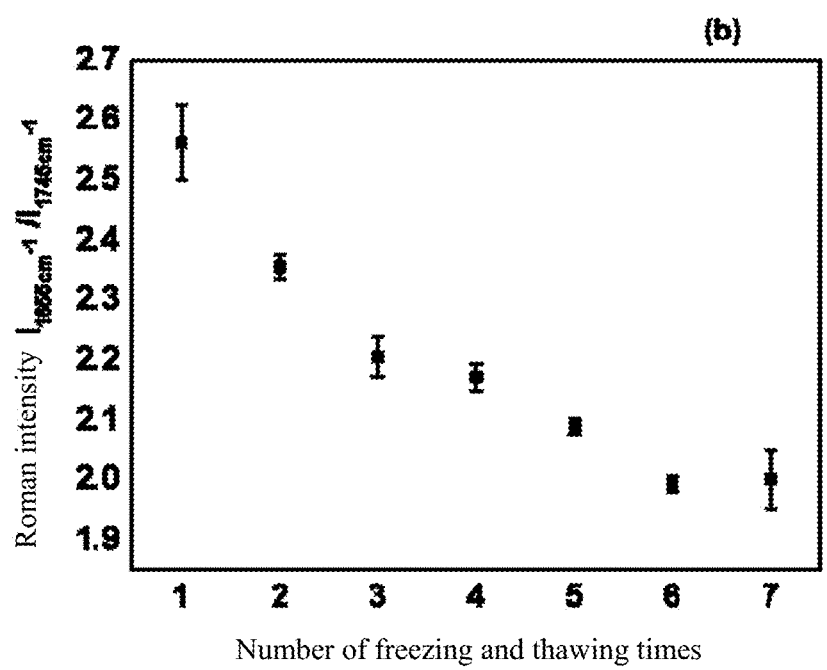

See FIGS. 1a-1c (peroxide value data of part of the freezing and thawing groups in the embodiments and the comparison groups are too low and consequentially cannot be detected through the national standard method) and the following table 1, the implementation result shows that along with the increment of the number of freezing and thawing times, the peroxide value, the TBARS and the acid value are increased gradually. It indicates that with the increment of the number of freezing and thawing times, the quality of beef fat deteriorates. Meanwhile, see FIG. 2a-2b (the solid lines represent the freezing and thawing groups in the embodiments, and the dotted lines represent the comparison groups), FIGS. 3a-3b and the following table 1, according to the change of the Raman spectrum, with the increment of the number of the freezing and thawing times, the peak intensity 970 $cm^{-1}$ and the peak intensity 1080 $cm^{-1}$ are decreased gradually, and the peak intensity 1068 $cm^{-1}$ and the peak intensity 1125 $cm^{-1}$ are increased gradually. In addition, with increment of freezing and thawing times, the peak value ratios $I_{1655}/I_{1745}$ and $I_{1655}/I_{1442}$ are decreased gradually.

See the following table 1, it can be known through correlation analysis between the fat quality evaluation indexes and the Raman spectrum that the influences of repeated freezing and thawing on the quality change process of beef fat can be represented rapidly and accurately through the Raman spectrum.

TABLE 1

Correlation analysis between the fat quality evaluation indexes and Raman spectrum

| | Fat Quality Evaluation Index[1] | | | Raman Spectrum | |
|---|---|---|---|---|---|
| | Peroxide Value | TBARS | Acid Value | $I_{1652cm-1}/I_{1740\,cm-1}$ | $I_{1652cm-1}/I_{1442\,cm-1}$ |
| Peroxide Value | 1 | 0.868 | 0.887 | −0.928 | −0.825 |
| TBARS | / | 1 | 0.891 | −0.860 | −0.791 |
| Acid Value | / | / | 1 | −0.885 | −0.862 |
| $I_{1652cm-1}/I_{1740\,cm-1}$ | / | / | / | 1 | 0.902 |
| $I_{1652cm-1}/I_{1442\,cm-1}$ | / | / | / | / | 1 |

It should be understood that the above preferred embodiments are only used for illustrating the content of the invention, other embodiments of the invention are available besides the above preferred embodiments, and all technical schemes formed by equivalent substitutes or equivalent transformations made by those skilled in the field based on the content and technical inspiration of the invention are within the protection scope of the invention.

What is claimed is:

1. A method for representing the quality change process of beef fat during repeated freezing and thawing through a Raman spectrum, comprising:
    setting operating parameters of a laser Raman spectrometer, wherein the operating parameters include wavelength of exciting light, laser power and scanning time;
    freezing and thawing beef repeatedly, then extracting fat of the thawed beef, and afterwards conducting Raman spectrum scanning on the extracted fat;
    analyzing and processing an obtained original Raman spectrum, so that the quality change process of beef fat during repeated freezing and thawing is represented,
    wherein in the process of repeatedly freezing and thawing the beef, the beef is frozen for over 24 hours at the temperature of −18 to −20° C. and then thawed at the temperature of 2 to 4° C. until the center temperature of the beef reaches 2 to 4° C., so that one freezing and thawing cycle is completed.

2. The method according to claim 1, characterized in that the wavelength of the exciting light is set to 785 nm, the laser power is set to 50~500 mw, and the scanning time is set to 5~20 s.

3. The method according to claim 1, characterized in that extracting beef fat comprises the sub-steps of mincing the thawed beef, mixing and oscillating an extraction agent and the minced beef, and then removing the extraction agent through rotary evaporation to extract the fat, wherein the extraction agent includes petroleum ether.

4. The method according to claim 1, characterized in that analyzing the obtained original Raman spectrum comprises the sub-step of conducting background deduction on the obtained original Raman spectrum, and conducting normalization through the Raman peak 1442 $cm^{-1}$, so that a normalized Raman spectrum is obtained.

5. The method according to claim 4, characterized in that analyzing the obtained original Raman spectrum further comprises the sub-step of measuring the changes of the peak intensities of selected characteristic peaks in the normalized Raman spectrum, so that the quality change process of the beef fat during repeated freezing and thawing is represented.

6. The method according to claim 5, characterized in that the selected characteristic peaks include the characteristic peak 970 $cm^{-1}$, the characteristic peak 1080 $cm^{-1}$, the characteristic peak 1068 $cm^{-1}$, the characteristic peak 1125 $cm^{-1}$, the characteristic peak 1655 $cm^{-1}$ and the characteristic peak 1745 $cm^{-1}$, wherein the peak intensities of the characteristic peak 970 $cm^{-1}$, the characteristic peak 1080 $cm^{-1}$ and the characteristic peak 1655 $cm^{-1}$ are decreased gradually along with the increment of the number of freezing and thawing times of the beef, and the peak intensities of the characteristic peak 1068 $cm^{-1}$ and the characteristic peak 1125 $cm^{-1}$ are increased gradually along with the increment of the number of freezing and thawing times of the beef.

7. The method according to claim 4, characterized in that analyzing the obtained original Raman spectrum further comprises the sub-step of measuring the changes of selected peak intensity ratios in the normalized Raman spectrum, so that the quality change process of the beef fat during repeated freezing and thawing is represented.

8. The method according to claim 7, characterized in that the selected peak intensity ratios include $I_{1655}/I_{1745}$ and $I_{1655}/I_{1442}$, wherein $I_{1655}$ is the peak intensity of the Raman peak 1655 $cm^{-1}$, $I_{1745}$ is the peak intensity of the Raman peak 1745 $cm^{-1}$, $I_{1442}$ is the peak intensity of the Raman peak 1442 $cm^{-1}$, and $I_{1655}/I_{1745}$ and $I_{1655}/I_{1442}$ are decreased gradually along with the increment of the number of freezing and thawing times of the beef.

* * * * *